(12) United States Patent
Siwak et al.

(10) Patent No.: US 7,465,397 B2
(45) Date of Patent: *Dec. 16, 2008

(54) PROCESS FOR REMOVING PROTEIN AGGREGATES AND VIRUS FROM A PROTEIN SOLUTION

(75) Inventors: Martin Siwak, Topsfield, MA (US); Hong An, Acton, MA (US); Jason R. Comier, Westford, MA (US); Dana Kinzlmaier, Acton, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/489,232

(22) Filed: Jul. 19, 2006

(65) Prior Publication Data
US 2006/0249455 A1   Nov. 9, 2006

Related U.S. Application Data

(62) Division of application No. 10/357,914, filed on Feb. 4, 2003, now Pat. No. 7,118,675.

(60) Provisional application No. 60/354,386, filed on Feb. 4, 2002.

(51) Int. Cl.
*B01D 11/00* (2006.01)
*B01D 61/00* (2006.01)
*C02F 1/42* (2006.01)
*C12N 5/04* (2006.01)
*C02K 16/00* (2006.01)

(52) U.S. Cl. ............... 210/645; 210/650; 210/651; 210/661; 210/198.1; 435/239; 435/415; 435/412; 530/390.1

(58) Field of Classification Search .......... 210/645, 210/500.37, 650–651, 767, 656, 660–661, 210/635, 198.1, 636; 530/390.1, 412, 415; 435/239

See application file for complete search history.

(56) References Cited

U.S. PATENT DOCUMENTS 4,618,533 A   10/1986   Steuck (Continued)

FOREIGN PATENT DOCUMENTS

DE   10114537   10/2002

(Continued)

OTHER PUBLICATIONS

Honig et al, Impact of Design and Selection of Prefilters s on Operating Cost, Filtration and Separation, Gbelsevier Advanced Technology, Oxgord, vol. 34, 1997, pp. 73-78.

*Primary Examiner*—Ana M Fortuna

(57) ABSTRACT

A process is provided for selectively removing protein aggregates from a protein solution in a normal flow (NFF) filtration process. Preferably, it relates to a process for selectively removing protein aggregates from a protein solution in a normal flow (NFF) filtration process and virus particles from a protein solution in a two-step filtration process. In a first step, a protein solution is filtered through one or more layers of adsorptive depth filters, charged or surface modified microporous membranes or a small bed of chromatography media in a normal flow filtration mode of operation, to produce a protein aggregate free stream. The aggregate free protein stream can then be filtered through one or more ultrafiltration membranes to retain virus particles at a retention level of at least 3 LRV and to allow passage therethrough of an aggregate free and virus free protein solution.

14 Claims, 3 Drawing Sheets

U.S. PATENT DOCUMENTS

| | | | |
|---|---|---|---|
| 5,085,784 A | 2/1992 | Ostreicher | |
| 5,464,818 A | 11/1995 | Yamaguchi et al. | |
| 5,466,377 A | 11/1995 | Grandics et al. | |
| 5,547,576 A | 8/1996 | Onishi et al. | |
| 5,629,084 A | 5/1997 | Moya | |
| 5,958,244 A * | 9/1999 | Hartmann | 210/650 |
| 6,117,423 A | 9/2000 | Berg | |
| 6,193,891 B1 | 2/2001 | Kent et al. | |
| 6,281,336 B1 | 8/2001 | Laursen et al. | |
| 6,365,395 B1 | 4/2002 | Antoniou | |
| 6,387,877 B1 | 5/2002 | More et al. | |
| 6,498,240 B1 | 12/2002 | Leonard et al. | |
| 6,630,195 B1 | 10/2003 | Muralidhara et al. | |
| 6,806,355 B2 | 10/2004 | Joergensen et al. | |
| 7,108,791 B2 * | 9/2006 | Tkacik et al. | 210/651 |
| 7,118,675 B2 * | 10/2006 | Siwak et al. | 210/645 |

FOREIGN PATENT DOCUMENTS

| | | |
|---|---|---|
| EP | 1203774 | 5/2002 |
| WO | WO 97/32893 | 9/1997 |
| WO | WO 97/45140 | 12/1997 |
| WO | WO 99/19343 | 4/1999 |
| WO | WO 03/066669 | 8/2003 |

* cited by examiner

PROCESS FOR REMOVING PROTEIN AGGREGATES AND VIRUS FROM A PROTEIN SOLUTION

CROSS-REFERENCE TO RELATED APPLICATIONS

The present application is a divisional patent application of U.S. application Ser. No. 10/357,914, filed on Feb. 4, 2003 which claims the benefit of U.S. Provisional Application No. 60/354,386, filed on Feb. 4, 2002.

BACKGROUND OF THE INVENTION

This invention relates to a process for selectively removing protein aggregates from a protein solution. More particularly, this is invention relates to a process for selectively removing protein aggregates and virus from a protein solution.

Plasma derived protein solutions such as immunoglobulin protein (IgG,) and other proteins (natural or recombinant) such as monoclonal antibodies routinely contain protein aggregates comprising protein trimers or higher polymers. In order to administer this solution to a patient, it is necessary to first remove these aggregates to avoid a toxic response by the patient. When utilizing conventional filtration processes, aggregates are undesirable since the filter, especially the viral clearance filter, rapidly becomes plugged by the aggregates even at low aggregate concentrations of 0.01-0.1%. Accordingly, it has been necessary to utilize expensive gel chromatography or size exclusion chromatography processes to effect selective aggregate removal. Alternatively, one can use an ultrafiltration membrane operated in a constant diafiltration mode to effect aggregate removal, See U.S. Ser. No. 09/706,003, filed Nov. 3, 2000.

Viruses also are a potential contaminant in parenteral and other solutions containing a protein that is derived from either whole organisms or mammalian cell culture sources. Currently several chemical and physical methods exist to inactivate virus. These methods are not generic to all viruses equally and some operate at the expense of protein activity. For example, heat pasteurization is used in solutions where protein denaturization can be minimized through the addition of stabilizers. In the biotechnology industry, strategies have been adopted that combine several inactivation or removal steps in the downstream process to maximize virus removal capability and protein recovery. The operations used are generally those operations optimized to purify the parenteral product and are validated for the virus removal capability. Thus, virus removal is an additional capability from a by-product of normal operation. Finally, at the end of the process, steps such as chromatography, filtration or heat may be added to increase overall virus clearance. This strategy has two shortcomings; (1) the virus clearance of these operations may not apply to putative virus that cannot be assayed; and (2) the virus clearance of the process needs to be monitored continually. It is necessary to remove virus at a log retention value at least 3, i.e., at least about 99.9% removal.

Accordingly, it would be desirable to provide a process for removing protein aggregates from a protein solution by a filtration process that avoids premature plugging of the filtration device utilized in the process. In addition, it would be desirable to provide such a process that can be utilized in conjunction with a process for removing virus from the protein solution at a log retention value of at least 3.

SUMMARY OF THE INVENTION

The present invention provides a process for removing protein aggregates comprising protein trimers and higher protein polymers from a protein solution. The protein solution containing the aggregates are filtered through filtration media such as one or more layers of fibrous filtration media or charged or surface modified microporous membranes, or a small bed of chromatography media such as ion exchange material to selectively bind the agglomerates and remove them from the liquid stream. Filtration is effected using a dead end (normal) filtration (NFF) filter device. When filtering a protein solution containing virus, the viral filter can be utilized downstream of the aggregate removal filter to retain virus particles. The aggregate removal filter is disposed of after use.

When utilizing a second filtration step to selectively retain virus, filtration can be effected with one or more ultrafiltration membranes either by tangential flow filtration (TFF) or by dead end (normal) filtration (NFF) wherein an agglomerate and viral free stream is produced. The one or more ultrafiltration membranes retain virus particles while permitting passage of protein monomer there through. Subsequent to the TFF viral filtration step, the membrane can be flushed with water or an aqueous buffer solution to recover any protein retained by the membrane. While utilizing NFF, the protein passes through the filter while the virus particles are retained within the filter upstream of the membrane.

The use of the preferred two-step process of this invention to remove protein aggregates and virus particles from a protein solution provides substantial advantages over the filtration processes of the prior art. Since the device of the first step (removing aggregates) is operated in the normal flow mode, it may be disposable and there is no cleaning process that would be subject to validation procedures and the like. In addition, the normal flow mode of operation is less expensive to purchase and operate, as little capital needs to be expended to set up such a system as compared to a TFF ultrafiltration type system. Further, since the membrane utilized in the second step of removing virus particles does not foul with protein aggregates, its useful life is extended since it does not become plugged with protein aggregates.

It is an object of the present invention to provide a process for selectively removing protein aggregates from an aqueous solution of proteins which comprises:

filtering a protein solution containing said protein aggregate through an adsorptive depth filter, a charged or surface modified microporous layer or layers in a normal flow filtration mode of operation, and recovering the aggregate free protein solution.

It is another object of the present invention to provide a process for selectively removing protein aggregates from an aqueous solution of proteins which comprises:

filtering a protein solution containing said protein aggregate through an adsorptive depth filter, a charged or surface modified microporous layer or layers in a normal flow filtration mode of operation, recovering the aggregate free protein solution and filtering said protein solution through one or more ultrafiltration membranes having a molecular weight cut off of between about 200 kD and about 1000 kD to retain virus particles in said one or more ultrafiltration membranes at a level of at least 3 LRV, and to recover an aqueous, virus-free protein solution.

It is a further object of the present invention to provide a process that removes protein aggregates from a protein stream in a normal (NFF) flow filtration mode.

It is an additional object of the present invention to provide a process that removes protein aggregates from a protein stream in a normal (NFF) flow filtration mode followed by a viral removal step in a normal (NFF) flow filtration mode.

It is another object of the present invention to provide a process that removes protein aggregates from a protein stream in a normal (NFF) flow filtration mode followed by a viral removal step in a tangential (TFF) flow filtration mode.

DESCRIPTION OF SPECIFIC EMBODIMENTS

In accordance with a preferred embodiment of this invention, a protein solution is first filtered with a retentive media to selectively retain protein aggregates comprising protein trimers and higher protein polymers while permitting passage of protein monomers therethrough. A portion of protein dimers in the protein solution are retained by the membrane while a portion of protein dimers in solution are passed through the membrane. This filtration step is effected using a device of one or more layers of a fibrous media, one or more layers of charged or surface modified microporous membranes or a small bed of chromatography media. When utilizing these materials, substantially complete protein aggregate removal is effected while permitting recovery of greater than about 85% protein monomer, preferably greater than about 90% protein monomer.

Figure 1:
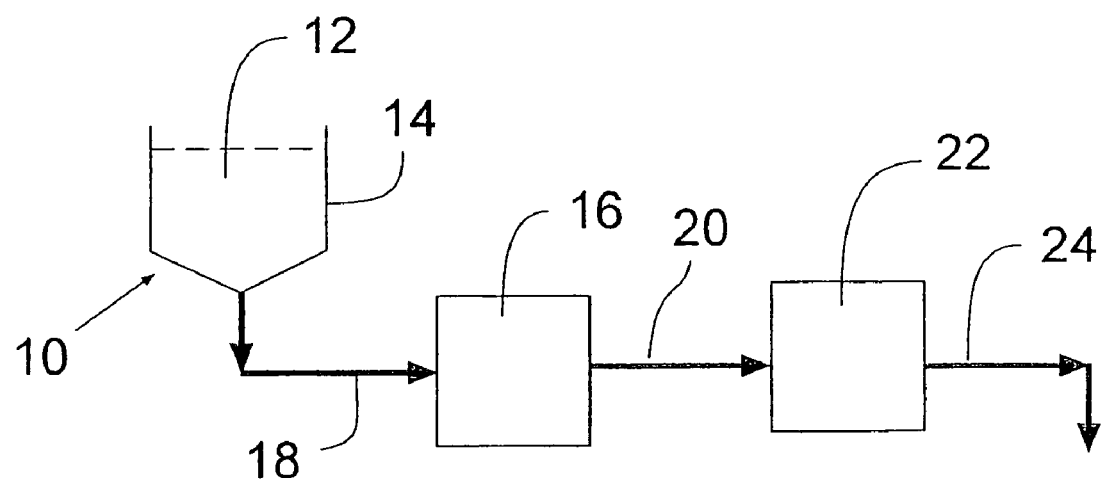
FIG. 1 is a flow diagram illustrating a first preferred embodiment of the process of this invention.

In the first stage 10 of the one preferred embodiment of the process of this invention as shown in FIG. 1 one utilizes a constant pressure mode of filtration. A protein solution 12 is retained by pressurized reservoir 14 and is pumped to the filtration media unit 16 by the pressure in the tank through conduit 18. The solution is subjected to a normal flow mode of filtration with the aggregates being retained by the media and the aggregate free solution discharged as the filtrate from the first step 10. The filtrate is passed through conduit 20 for further downstream processing such as the second step of filtration 22 (explained in detail below) and then to an outlet conduit 24. By operating in this manner, protein aggregates are retained by media unit 16 while protein monomer is passed through media 16.

Alternatively, one could use a pump to create the constant pressure of the system although it is not preferred as the pump output would need to be carefully controlled to a constant pressure via valves or pump speed and would require a feedback system to ensure that the pressure is kept constant.

Figure 2:
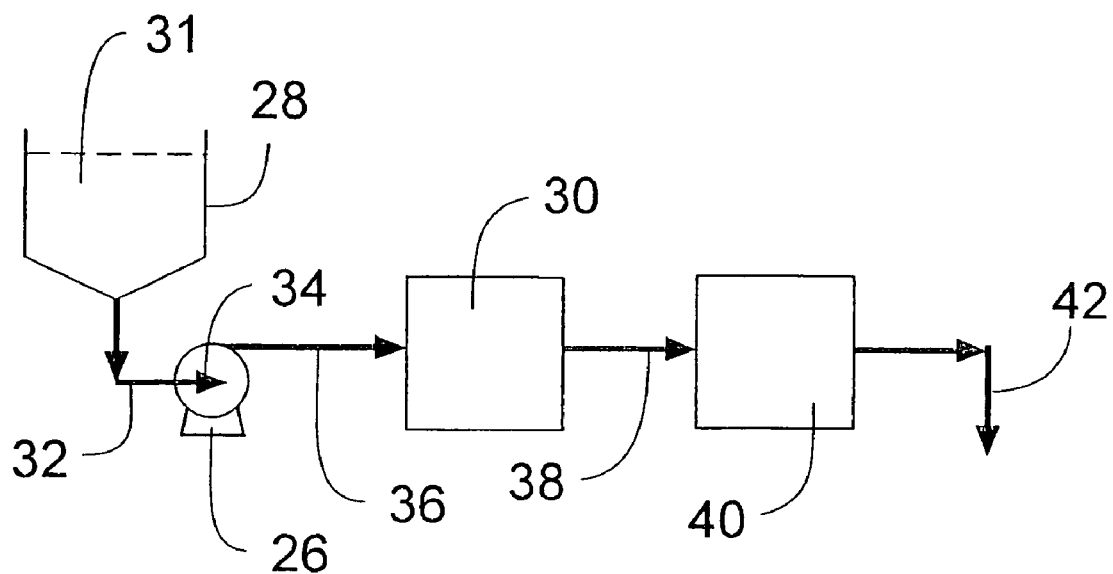
FIG. 2 is a flow diagram illustrating another preferred embodiment of the process of this invention.

A second embodiment of the present invention is shown in FIG. 2 in which a constant flow mode of operation is used. In this system one uses a pump 26 located between the reservoir 28 (typically a non-pressurized as compared to the pressurized vessel of the embodiment of FIG. 1) and the first filtration step 30 to maintain the constant flow. The solution 31 is pumped through conduit 32 to the pump inlet 34 and then pumped through conduit 36 to the first filtration step 30. Again the filter of the first step 30 may any of those mentioned above in the discussion of FIG. 1. The solution is subjected to a normal flow mode of filtration with the aggregates being retained by the filter of the first step 30 and the aggregate free solution discharged as the filtrate from the first step 30. The filtrate is passed through conduit 38 for further downstream processing such as the second step of filtration 40 (explained in detail below) and then to an outlet conduit 42. If one desires, one can add a recirculation loop (not shown) at the outlet (not shown) of the first filtration step and recirculate the filtrate through the filtration step one or more additional times to further reduce the aggregate level in the filtrate. Use of a valve (not shown) is the simplest means for controlling the flow between the recirculation loop and the downstream conduit. It has been found that one recirculation pass is sufficient. Additional recirculation passes are generally unnecessary and increase manufacturing time and costs unnecessarily.

In the second filtration step (22 or 40), one conducts a viral removal filtration after the removal of aggregate removal. Viruses are removed from the aggregate free solution by either a normal flow filter (NFF) or a tangential flow filtration (TFF) filter such as is described in U.S. Ser. No. 09/706,003, filed Nov. 3, 2000, now U.S. Pat. No. 6,365,395.

Representative suitable devices for the first step include those formed from fibrous media formed of cellulosic fibers, synthetic fibers or blends thereof, such as MILLISTAK®+ pads available from Millipore Corporation of Bedford, Mass.; microporous membranes which are either charged or have a surface chemistry (such as hydrophilicity or hydrophobicity or a positive or negative charge as are taught by U.S. Pat. Nos. 5,629,084 and 4,618,533) made from a material selected from the group consisting of regenerated cellulose, polyethersulfone, polyarylsulphone, polysulfone, polyimide, polyamide or polyvinylidenedifluoride (PVDF), such as charged Durapore® membrane, hydrophobic Durapore® membrane, hydrophobic Aervent® membrane and Intercept™ Q quaternary charged membrane, all available from Millipore Corporation, Bedford, Mass.; and chromatography media including size exclusion media, ion exchange media, hydrophobic media and the like such as Cellufine® hydrophobic media, PEI-1000 media, Cellufine® ion, exchange, and Matrex® chromatography media available from Millipore Corporation, Bedford, Mass., USA.

Filtration can be effected with one or a plurality of devices wherein the feed protein solution is contacted with the devices in parallel or series flow.

When removing virus from a protein solution substantially free of protein aggregates, the filtrate from the aggregate removal step is directed to a second membrane filtration step. The second filtration step utilizes one of more viral filtration (typically ultrafiltration) membranes that can be conducted either in the TFF mode or the NFF mode. In either mode, the filtration is conducted under conditions to retain the virus, generally having a 20 to 100 nanometer (nm) diameter, on the membrane surface while permitting passage of protein monomer and a portion of protein dimer through the membrane. In addition, when filtration of the feed stream is completed, the membrane is flushed with water or an aqueous buffer solution to remove any retained proteins. The use of the flushing step permits obtaining higher yields of protein solution substantially free of virus.

Representative suitable ultrafiltration membranes which can be utilized in the virus removal step include those formed from regenerated cellulose, polyethersulfone, polyarylsulphones, polysulfone, polyimide, polyamide, polyvinylidenedifluoride (PVDF) or the like and are known as VIRESOLVE® membranes and RETROPORE™ membranes available from Millipore Corporation of Bedford, Mass. These can be supplied in either a cartridge (NFF) form, such as VIRESOLVE® NFP viral filters, or as cassettes (for TFF), such as PELLICON® cassettes, available from Millipore Corporation of Bedford, Mass.

The viral filters utilized in the process of this invention are characterized by a log retention value (LRV; the negative logarithm of the sieving coefficient) for virus particles and other, particles that increase monotomically with the diameter of the particle; in the size range of interest for virus of 20 to 100 nm diameter. Empirically, the LRV increases continuously with the size of the particle projected area (the square of the particle diameter). Where one is concerned with removing small sized virus particles from protein solution, satisfactory LRV of at least about 3 are obtained. However, the molecular weight cutoff is reduced thereby reducing protein recovery. Therefore, the user will choose a membrane that gives satisfactory LRV and protein recovery. In any event, the membranes utilized in the process of this invention are capable of producing an LRV for virus of 3 and can extend to as high as about 8 or greater where the virus particle size is between a 10 and 100 nm diameter. In addition, the virus removal membranes utilized in the process of this invention are characterized by a protein molecular weight cut off of between about 500 and 1000 kilo Daltons (kD). In all cases, the empirical relationship with particle projected area is retained. Log reduction values for virus particles (single solutes in solution; in absence of protein) depends upon the virus particle size. With small sized virus such as hepatitis, an LRV of greater than about 3 can be obtained and with larger sized virus such as the AIDS virus, a LRV of greater than 6 can be obtain for example.

The following example illustrates the present invention and is not intended to limit the same.

EXAMPLE I

An IgG aggregate feed solution (SeraCare 5% Human Gamma Globulin, available from SeraCare, Inc., Cat#HS-9000) was added to a phosphate buffer (10 g/L Difco FA buffer, pH 7.2, from Fisher Scientific, Cat#DF 2314150) and EDTA (10 mM ethylenediamine tetra acidic acid, disodium-calcium salt available from Sigma Aldrich, cat#ED2SC).

The aggregate feed solution was then modified to represent a 10% aggregate load by filtering 90% of the feed through a membrane that removed the protein aggregate (PLCXK membrane as cellulose UF membrane with a nominal molecular cutoff of 1000 kDaltons available from Millipore Corporation of Bedford, Mass.)

Figure 3:
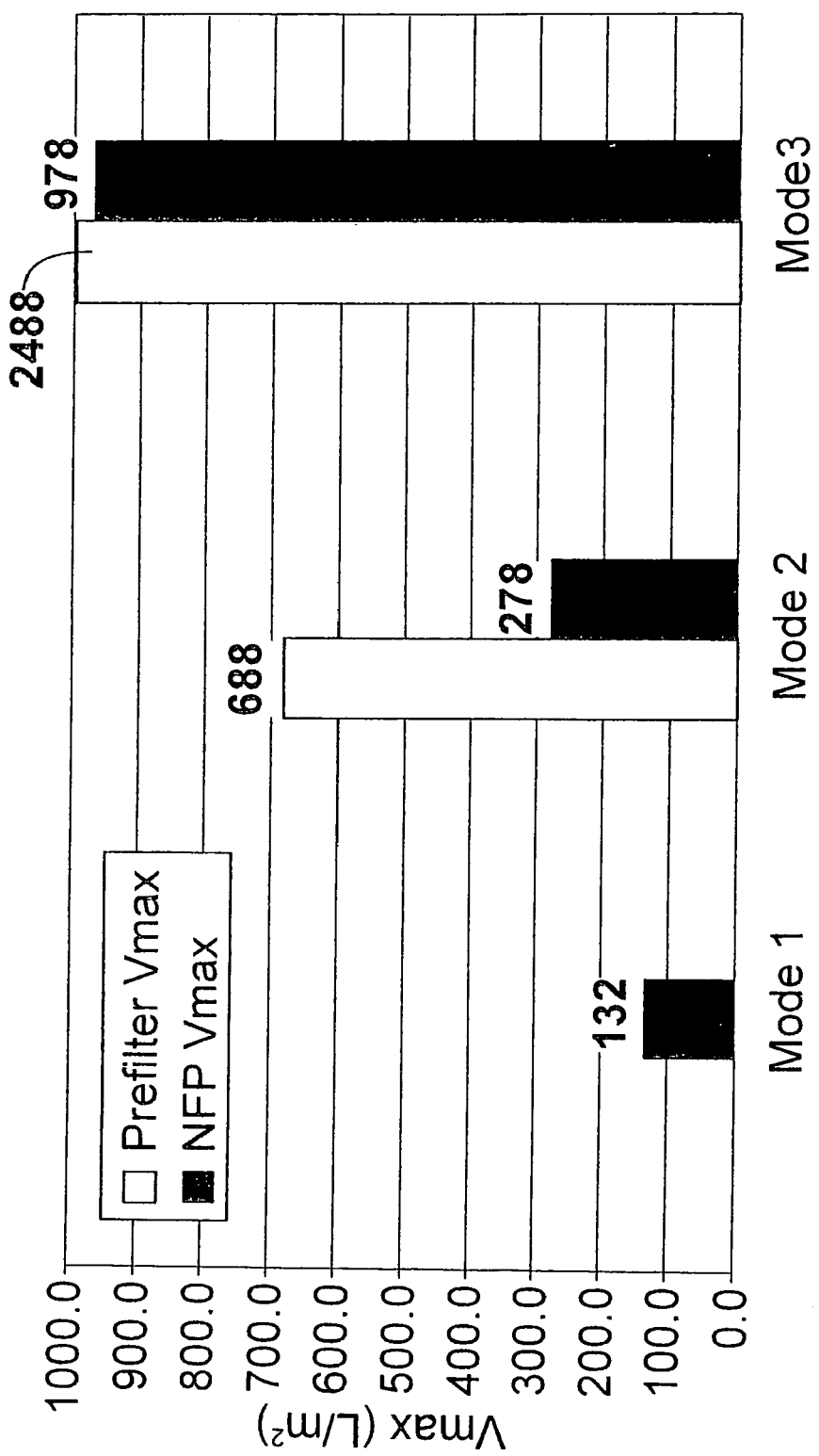
FIG. 3 is a chart of the VMAX of three different processes, the first of the prior art and the other two of embodiments of the present invention.

FIG. 3 shows the throughput results (liters of fluid processed/square meter of material before clogging of the material occurs) on the aggregate feed solution at 10% aggregates by three different modes of operation.

Mode #1 used the conventional normal flow viral filter without any aggregate removal step using a VIRESOLVE® NFP viral filter of 13.5 cm² available from Millipore Corporation of Bedford, Mass. was provided for selectively removing protein aggregates from a protein solution in a normal flow (NFF) filtration process.

Mode #2 used the first embodiment of the present invention using a MILLISTAK® 75DE Grade device available from Millipore Corporation of Bedford, Mass. having 13.0 square centimeters of media. The filter is composed of charged fibrous cellulose media. This was followed by a viral removal step using VIRESOLVE® NFP filter of 13.5 cm² available from Millipore Corporation of Bedford, Mass.

Mode #3 used another embodiment of the present invention using a MILLISTAK®75DE Grade device available from Millipore Corporation of Bedford, Mass. having 13.0 square centimeters of media. The filter was composed of charged fibrous cellulose media having 13.0 cm² of media, in which the filtered fluid was then run through the media a second time, followed by a viral removal step using a VIRESOLVE® NFP filter of 13.5 cm² available from Millipore Corporation of Bedford, Mass.

FIG. 3 and Table 1 (below) show the Vmax (throughput) of the example. Mode #1 represents no aggregate removal step. Modes 2 and 3 represent different experiments run on different days with different batches of feed material.

Overall one can see the dramatic improvement in throughput and flux obtained with the NFF aggregate removal step. The Vmax was 200% greater than that of the Vmax obtained without the NFF.

The present invention provides a simple means for the removal of protein aggregates from a protein stream before viral filtration or other steps in the process. This reduces the fouling and clogging that would otherwise occur, increasing throughput and flux dramatically. Additionally, this is done with the need for tangential flow filtration (TFF) that is more costly to purchase and to run and which needs to be cleaned between uses. The present invention allows one to dispose of the aggregate filter allowing one to eliminate the cost of cleaning and storing the membrane between uses and the cost and time of validating one's procedures in doing so to regulatory agencies such as the FDA.

What is claimed:

1. A process for viral filtration of a protein containing stream comprising:
   (a) providing a filtration system comprising: (i) a pressurized reservoir comprising a solution which comprises one or more protein aggregates and viruses; (ii) a first conduit connecting the reservoir to a first filtration step comprising a device selected from the group consisting of one or more layers of adsorptive depth filters and one or more layers of charged or surface modified microporous membranes; (iii) a second conduit from the first filtration step to a second filtration step comprising one or more ultrafiltration membranes having a molecular weight cut off of between about 200 kD and about 1000 kD to retain virus particles in said one or more ultrafiltration membranes at a level of at least 3 LRV; and
   (d) an outlet conduit connected to the second filtration step;
   (b) pumping the solution from the pressurized reservoir through the first conduit to the first filtration step;
   (c) running the first filtration step in a normal flow filtration mode with the one or more protein aggregates and viruses being retained by the first filtration step;
   (d) discharging the solution from the first filtration step to the second conduit;
   (e) passing the solution from the second conduit through the second filtration step; and
   (f) discharging the solution from the second filtration step to the outlet conduit.

2. The process of claim 1 wherein the process is run in a constant pressure mode of operation.

3. The process of claim 1 further comprising the step of flushing retained protein from said one or more ultrafiltration membranes.

4. The process of claim 1 wherein the filtration is through one or more layers of adsorptive depth filters.

5. The process of claim 1 wherein the filtration is through one or more layers of one or more layers of charged or surface modified microporous membranes.

6. The process of claim 1 wherein the filtration is through one or more layers of adsorptive depth filters made of a material selected from the group consisting of cellulosic fibers, synthetic fibers and blends thereof.

7. A process for the viral filtration of a protein containing stream comprising:
(a) providing a filtration system comprising a non-pressurized reservoir comprising a solution which comprises one or more protein aggregates and viruses; (ii) a first conduit connecting the reservoir to a pump, wherein the pump is connected to a second conduit which connects the pump to a first filtration step comprising a device selected from the group consisting of one or more layers of adsorptive depth filters and one or more layers of charged or surface modified microporous membranes; (iii) a third conduit from the first filtration step to a second filtration step comprising one or more ultrafiltration membranes having a molecular weight cut off of between about 200 kD and about 1000 kD to retain virus particles in said one or more ultrafiltration membranes at a level of at least 3 LRV; and (iv) an outlet conduit from the second filtration step;
(b) pumping the solution from the reservoir through the first conduit to the pump and from the pump through the second conduit to the first filtration step;
(c) running the first filtration step in a normal flow filtration mode with the one or more protein aggregates and viruses being retained by the first filtration step;
(d) discharging the solution from the first filtration step to the third conduit;
(e) passing the solution from the third conduit through the second filtration step in a normal flow filtration mode; and
(f) discharging the solution from the second filtration step to the outlet conduit.

8. The process of claim 7 wherein the process is run in a constant flow mode of operation.

9. The process of claim 7 further comprising the step of flushing retained protein from said one or more ultrafiltration membranes.

10. The process of claim 7 wherein filtration with said one or more ultrafiltration membranes is effected by tangential flow filtration.

11. The process of claim 7 wherein filtration with said one or more ultrafiltration membranes is effected in a normal flow filtration mode of operation.

12. The process of claim 7 wherein the first filtration step is through one or more layers of adsorptive depth filters.

13. The process of claim 7 wherein the first filtration step is through one or more layers of charged or surface modified microporous membranes.

14. The process of claim 7 wherein the first filtration step is through one or more layers of adsorptive depth filters made of a material selected from the group consisting of cellulosic fibers, synthetic fibers and blends thereof.

* * * * *